(12) United States Patent
Starcher

(10) Patent No.: US 7,608,126 B1
(45) Date of Patent: Oct. 27, 2009

(54) METHOD FOR HORTICULTURE PLANT REJUVENATION

(76) Inventor: Robert C. Starcher, 45 Adams Way, Sayville, NY (US) 11782

( * ) Notice: Subject to any disclaimer, the term of this patent is extended or adjusted under 35 U.S.C. 154(b) by 384 days.

(21) Appl. No.: 11/729,570

(22) Filed: Mar. 29, 2007

Related U.S. Application Data

(60) Provisional application No. 60/789,030, filed on Apr. 4, 2006.

(51) Int. Cl.
*C05F 11/10* (2006.01)

(52) U.S. Cl. .................. 71/11; 71/31; 71/33; 71/53; 71/64.1

(58) Field of Classification Search .............. 71/11–63, 71/64.1; 47/58.1 R
See application file for complete search history.

(56) References Cited

U.S. PATENT DOCUMENTS

| 6,623,780 B1 | 9/2003 | Stevens et al. |
| 2003/0049689 A1 | 3/2003 | Edwards |

OTHER PUBLICATIONS

Adams, W., Green, K., Johnson, M. H., Kearse, E. C., Lathe, R., McIntyre O. L., and Phillips, C. I. Influence of Dehydroepiandrosterone on Rabbit Intraocular Pressure. (2001). pp. 42-47. vol. 33, No. 1. http://content.karger.com.
Follett, R. H., Fertigation. (2006). No. 0.512. http://www.ext.colostate.edu/PUBS/CROPS/00512.html.
Busman, L., Lamb, J., Randall, G., Rehm, G., and Schmitt, M. The Nature of Phosphorus in Soils. (2002). Regents of the University of Minnesota. http://www.extension.umn.edu/distribution/cropsystems/DC6795.html.
Vitosh, M. L., MSUE Agricultural Extension Bulletin: N-P-K Fertilizers. (2005). http//:www.canr.msu.edu/vanburen/e-896.htm.
Liquid Fertilizers. (1999). http://www.prolawnsystems.com/liquid_fertilizers1.htm.
Math and Science Activity Center: Solutions, Suspensions and Colloids—Summary. (1999). http://www.edinformatics.com/math_science/solutions_suspensions_colloids.htm.
Griffith, B. Essential Role of Phosphorus (P) in Plants. (2001). http://www.agcentral.com/imcdemo/06Phosphorus/06-01.htm.
Reusch, W. Lipids. (2004).http://www.cem.msu.edu/~reusch/VirtTxtJml/lipids.htm.
Wolters-Arts, M., Van Der Weerd, L., Van Aelst, A. C., Van As, H., Van Der Weerd, J., and Mariani, C. Water-conducting properties of lipids during pollen hydration. (2002) pp. 513-519. vol. 25. Blackwell Science Ltd.
Heinemann, B., Andersen, K. V., Nielsen, P. R., Bech, L. M., and Poulsen, F. M. Structure in solution of a four-helix lipid binding protein. Protein Science. (1996). vol. 5., pp. 13-23. Cambridge University Press.
Chapter 26: Lipids. (2007). http://www.chem.ucalgary.ca/courses/351/Carey5th/Ch26/ch26-0.html.
McKell, C. M., and Wilson, A. M. Effects of Soil Moisture Stress on Absorption & Translocation of Phosphorus Applied to Leaves of Sunflowers. Plant Physiology. (1961). vol. 36, No. 6, pp. 762-765.
Chase, M. E. Phyto-Reaction Kinetics in Cash Crop Using Traditional & Non-traditional Plant Growth Regulators, Uniondale, High School, Dowling College Spring Science Fair, Oakdale, NY (May 30, 2002).
Math and Science Activity Center: Suspensions and Colloids. (2007). http://www.edinformatics.com/math_science/suspensions_colloids.htm.
Wikipedia. Permanent Wilting Point. (2007). http://en.wikipedia.org/wiki/Permanent_wilting_point.
Broadley, M. R. and White, P. J. Calcium in Plants. (2007). http://www.ncbi.nlm.nih.gov/entrez/query.fcgi?cmd=Retrieve&db=PubMed&list_uids=12....
Nature's Bounty: DHEA 25mg. Tablets(qty100). (2007). http://www.naturesbounty.com/pages/products.aspx?PID=123.

*Primary Examiner*—Wayne Langel
(74) *Attorney, Agent, or Firm*—Alfred M. Walker

(57) ABSTRACT

The present disclosure provides a plant rejuvenating agent using dehydroepiandrosterone (DHEA), or hydrates thereof, to form plant rejuvenating mixtures that may include additional components. The plant rejuvenating mixture including DHEA may be used in typical horticultural applications, including the improvement of soil fertility; the rejuvenation of unhealthy plants by providing both water for increased turgidity and sterols for plant cell repair; enhancing the longevity of growing season of plants; and retarding the senescence of fresh cut flowers.

51 Claims, No Drawings

METHOD FOR HORTICULTURE PLANT REJUVENATION

RELATED APPLICATIONS

This application is based in part upon provisional application 60/789,030 filed Apr. 4, 2006, and claims benefit and priority in part therefrom under 35 U.S.C. 119 (e). The content of provisional application 60/789,030 is expressly incorporated herein by reference.

This application is also based upon Applicant's Disclosure Document Number 587,757 dated Oct. 7, 2005.

FIELD OF THE INVENTION

This disclosure relates to a plant rejuvenating mixture, more specifically a combination that rejuvenates plants on the verge of the permanent wilting point, increases normal growth rate, and prolongs life span or growing season.

BACKGROUND OF THE INVENTION

Horticulture in the form of landscaping, floristry, and gardening, is a common pastime and occupation. In 1998, the United States recorded over ten billion dollars in horticultural sales. (http://www.nass.usda.gov/census/census97/horticulture/quickfacts/index.htm) The national gardening society reports that in 2005, 83% of all households participated in outdoor lawn and gardening activities. Also in 2005, lawn and garden retail sales totaled over 35 billion dollars. (http://www.gardenresearch.com/index.php?q=show&id=2602)

Beyond its current popular uses, horticulture also has therapeutic medical uses. A recent article reported "scientific studies with diverse populations, including residents of poor inner city neighborhoods, ecological restoration volunteers, and children with Attention Deficit/Hyperactivity Disorder. Moreover, the findings come from studies of diverse outcomes, including lower rates of violent and property crime, lower incidence of aggression, greater ability to cope with poverty, better life functioning, greater life satisfaction, reduced attention deficit symptoms, greater strength of community, and others." (Kuo, F. E. 2004. HORTICULTURE, WELL-BEING, AND MENTAL HEALTH: FROM INTUITIONS TO EVIDENCE. Acta Hort. (ISHS) 639:27-34 (http://www.actahort.org/books/639/639_2.htm)

Plant growth and therefore horticulture is dependent on a number of factors: soil quality, water availability, temperature, light, etc. Plants that are deprived of these factors will deteriorate, showing signs of wilting, withering, and at times becoming slimy. To prevent plant deterioration fertilizers are often used. Fertilizers are used to promote plant growth. They are typically composed of micro or macronutrients (or a combination thereof) and are either organic or inorganic. Macronutrients are present at a greater level in plants while micronutrients vary in concentration depending on the plant.

Fertilizers are also categorized as agricultural and horticultural. Agricultural fertilizers usual contain one or two macronutrients while horticultural fertilizers are a combination of macro and micronutrients. Horticultural fertilizers may be controlled or immediate release.

Fertilizers, both organic and inorganic, are used in horticultural and agricultural plant cultivation. While plants can at times be rejuvenated, the potential for that rejuvenation depends on the plants ability to quickly absorb the nutrients needed.

Phosphorus is a vital component for plants in structure and photosynthesis, and is needed for overall plant health and vigor, as noted in Griffith, "Essential Role of Phosphorus (P) in Plants", *Efficient Fertilizer Use*, IMC Agrico, 2006, 2 pages. See also Busman et al, "The Nature of Phosphorus in Soils," *Phosphorus in the Agricultural Environment*, University of Minnesota Extension, FO-06795-GO, 1998, 6 pages.

Calcium is also a vital component for plants. As noted in White; P J, Broadley, M R, "Calcium in Plants", Annals of Botany, 2003 October; 92(3): pp 487-511. Epub 2003 Aug. 21, "calcium is an essential plant nutrient", which is "required for various structural roles in the (plant) cell wall and membranes, it is a counter-cation for inorganic and organic anions in the (plant) vacuole, and the cystolic Ca2+ concentration" assists the plant in "numerous developmental cues and responses to environmental challenges."

In connection therewith, it is noted that wilting plants cannot utilize the macronutrient phosphorus as much as healthy, non-wilting plants. See Wilson and McKell, "Effect of Soil Moisture Stress On Absorption & Translocation of Phosphorus Applied to Leaves of Sunflower", *Plant Physiology*, 1961, November, Volume 36 (6), pages 762-765.

A certain amount of work has been done in the year 2002 on the use of DHEA with plants. This work by Monique E. Chase in "Photo-Reaction Kinetics in a Cash Crop Using Traditional & Nontraditional Plant Growth Regulators" (allen.dowling.edu/~chemistry/doc/sabstracts1.doc) examined the impact of DHEA as a plant growth regulator. Ms. Chase's use of DHEA was focused on soybeans and the use of DHEA as a growth regulator, in comparison to traditional plant growth regulators, such as indole-3-acetic acid (IAA). The present invention differs from that suggested by Ms. Chase in that it focuses on ornamental horticulture and the potential for rejuvenating deteriorated plants by combining DHEA with other necessary components of plant cell biology.

U.S. Patent publication 20030049689 of Edwards describes applying polypeptides in general to plant stems, leafs and vascular tissues, as well as to human and animal cells. Among the many polypeptides listed in Edwards includes DHEA.

SUMMARY OF THE INVENTION

The present invention preferably provides a method of rejuvenating a stressed and/or wilted plant, including the steps of:

a) providing a rejuvenating ingredient including,
  dehydroepiandrosterone (DHEA) or hydrates thereof, and
  preferably, essential plant nutrients of either or both of calcium and phosphorus, wherein said nutrients are supplied in an amount sufficient for plant rejuvenation;

b) adding said rejuvenating ingredient to a liquid selected from the group consisting of water and fertigation liquids, said liquid has optionally been heated;

c) forming a plant rejuvenating mixture, preferably as a colloidal dispersion or suspension, therefrom;

c) optionally, allowing the plant rejuvenating mixture to cool to a tepid level when hot liquid is used to form the plant rejuvenating mixture; and d) applying the plant rejuvenating mixture directly to the plant.

Optionally the heated water is cooled to room temperature, or cold water is added. Cold water is supplied optionally at about 55 to 60 degrees Fahrenheit, preferably at a temperature ranging from 40 to 75 degrees F.

The present invention is a plant rejuvenating mixture and a method for enhancing plant rejuvenation of wilted, stressed or diseased plants, which provides for contacting the plant or soil with a rejuvenating application of a plant rejuvenating mixture, such as a colloidal dispersion or a suspension. The plant rejuvenating mixture is comprised of DHEA and a liquid, preferably with the plant micronutrient calcium, such as from calcium carbonate and optionally with the addition of the macronutrient phosphorus, such as in combination with elemental calcium in dicalcium phosphate. In a preferred embodiment, hot water is used to enhance the plant rejuvenating mixture of water and DHEA, because DHEA is not very soluble in water. See E. Claire Kearse et al, "Influence of Dehydroepiandrosterone on Rabbit Intraocular Pressure," Ophthalmic Research 2001; 33:42-47 (DOI: 10.1159/000055640). Therefore the DHEA is preferably mixed in one of two generalized methods. In a first preferred embodiment, the DHEA is added to water, preferably supplied as hot water, to form the plant rejuvenating mixture, such as a colloidal dispersion or suspension, and then applied directly to a plant in distress, such as a wilted plant. In a second preferred embodiment, the DHEA is mixed with water to form an initial mixture that may be optionally heated and then added to a further quantity of water to dilute the initial mixture with water in a ratio of the initial mixture to a further quantity of water, in a ratio of from about 1:2 to 1:4. Although hot water is provided herein as a preferred liquid, it should be understood that an alternate embodiment may include the addition of very fine particulate DHEA with water provided at or below room temperature.

Preferably, the rejuvenating ingredient is derived from human consumable DHEA tablets, such as provided by Natrol, Inc. in an amount of 25 mg DHEA with 52 mg calcium carbonate and other inert components. In that case, the rejuvenating ingredient including DHEA mixed with calcium carbonate having 40 percent elemental calcium is mixed with water to form the plant rejuvenating mixture, such as a colloidal dispersion or a suspension, of DHEA and calcium to be applied to the stressed and/or wilted plant.

In another embodiment, the rejuvenating ingredient is derived from human consumable DHEA tablets, such as provided by Natures Bounty NBTY Corporation, in an amount of 5 mg DHEA with 38 mg dicalcium phosphate and other inert components. In that case, the rejuvenating ingredient including DHEA is mixed with water to form a plant rejuvenating mixture, such as a colloidal dispersion or a suspension, with dicalcium phosphate, having about 23 percent calcium and the remainder being a phosphate salt containing phosphorus and oxygen, to form the plant rejuvenating mixture of DHEA, calcium and phosphorus to be applied to the stressed and/or wilted plant, where the calcium is provided with phosphorus in the dicalcium phosphate.

Because calcium and/or phosphorus are essential plant nutrients, as noted by Griffith, supra and White, supra, it is believed that they act to provide essential plant nutrients to the stressed, diseased and/or wilted plant. However, because wilted plants cannot effectively utilize nutrients such as phosphorus, as per Wilson and McKell, supra, it is believed that the plant sterol DHEA provides cell rebuilding, while the infusion of water helps to rebuild turgidity to the plant tissues, while being repaired by the plant sterol DHEA, preferably with the addition of calcium and phosphorus nutrients. It makes sense that a plant on the verge of death may need to assimilate a molecule that is already built for it to use (i.e., a sterol, such as DHEA) rather than creating something itself from the building blocks while it's essentially on its death bed. The wilted plant needs a downstream product immediately, such as the plant sterol DHEA, but only when provided with water or other liquid to increase turgidity, so that the plant can then utilize the sterol and/or plant nutrients, such as calcium and/or phosphorus.

The method of preparing the plant rejuvenating mixture, such as a colloidal dispersion or a suspension, comprises optionally heating the liquid and then adding the DHEA to the liquid, optionally cooling the plant rejuvenating mixture to room temperature and then applying the plant rejuvenating mixture to the plant soil until saturation level is achieved.

The present invention operates on a different mechanism from currently utilized fertilizers. As dated above, current fertilizers operate by providing the ions involved in plant chemistry. The current invention enhances plant growth for horticultural plants by providing them with sterols that healthy plants can create from fertilizer ions but unhealthy plants need to have directly provided.

Phytosterols are found in all plants. They are the structural component of the cell membrane. By providing the wilting plant with water and the necessary cell wall component to create a turgid environment, such as the phytosterol DHEA, in combination with the micronutrient calcium, such as from calcium carbonate or dicalcium phosphate, and/or with the macronutrient phosphorus, such as from dicalcium phosphate, the plant is able to regain structure and continue its growth.

DETAILED DESCRIPTION

The present invention is a plant rejuvenating mixture and a method for enhancing plant growth, which provides for contacting the plant or soil with a rejuvenating application of the mixture. The plant rejuvenating mixture is composed of a rejuvenating ingredient including DHEA (dehydroepiandrosterone) or hydrates thereof (herein referred to generally as "DHEA") and a liquid selected from the group consisting of water and fertigation liquids. The liquid is optionally heated prior to or after the addition of the rejuvenating ingredient. The plant rejuvenating mixture is then optionally cooled to room temperature prior to addition to the plant soil. This plant rejuvenating mixture may be applied to plants, shrubs, bushes, cut flowers, and other plant materials as well as the surrounding soil to enhance and increase plant growth, rejuvenate plants and enhance plant proliferation. The compositions and methods may be applied to a variety of horticultural plants.

DHEA may be derived from the plant steroid, diosgenin, or more commonly may be manufactured synthetically. The application of DHEA in a mixture to plants may provide the plant with both water and cell wall components allowing the plant to restore turgid pressure and rejuvenate.

In one embodiment, aqueous plant rejuvenating mixtures comprising DHEA and methods for their use in soil amendment applications are provided. DHEA may be obtained from any convenient source, including vitamin manufacturers. Vitamin formulations of DHEA are often combined with micro and/or macronutrients such as calcium carbonate or dicalcium phosphate. These are primarily used as filling agents to produce tablets containing standardized doses of DHEA measurable in milligrams. The additional nutrients are of additional benefit to the plant's rejuvenation.

Although the rejuvenating ingredient including DHEA or hydrates thereof are preferably provided in the form of tablets, it should be understood that the DHEA or hydrates thereof may be provided in other physical forms. Therefore, the present invention is not intended to be restricted to the preferred tablet forms provided herein.

The rejuvenating ingredient including DHEA may be combined with a liquid to form a plant rejuvenating mixture. The liquid may typically be, but is not limited to, water, purified water, de-ionized water, and/or fertigation liquids. Fertigation liquids are liquid fertilizers generally known in the field of agriculture and horticulture. Fertigation liquids include, but are not limited to, anhydrous ammonia, aqua ammonia, N solutions and liquid mixed fertilizers. Liquid N-P-K fertilizers are also known as fluid fertilizer. Additional solid fertilizer and/or liquid fertilizer may be included to form the plant rejuvenating mixture. Optionally, the liquid is heated prior to the addition of rejuvenating ingredient including the DHEA. In a preferred embodiment, the rejuvenating liquid including DHEA is added while the liquid is hot and a plant rejuvenating mixture is formed. In this preferred embodiment, the plant rejuvenating mixture is allowed to cool to room temperature prior to addition to the plant soil. The plant rejuvenating mixture may typically include a ratio of DHEA to water of approximately 1:4 to 1:2 parts, and more preferably in a ratio of approximately 1:4 to 1:3. The ratios may be further varied to provide different concentrations, as desired, according to plant type; condition of the plant(s) at that time, and environmental conditions.

The DHEA may be taken up, or absorbed, in a plant rejuvenating mixture into a plant's transport system via the root system of the plant. The plant's transport system, including the xylem, brings the plant rejuvenating mixture into contact with the plant's cells. The plant rejuvenating mixture is then taken up into the cells via a currently unknown channel. Input of the DHEA into plant roots and shoots allows increased capacity for turgidity and growth, and with conventional fertilizers or suitable additives, such as calcium and phosphorus in the form of dicalcium phosphate, or calcium in the form of calcium carbonate, may support metabolic functions. Preferably the amount of dicalcium phosphate exceeds the amount of DHEA, such as, for example, in a ratio of about 7.6 to 1, where the dicalcium phosphate and DHEA are provided multiples of an amount of 38 mg of dicalcium phosphate and 5 mg of DHEA per unit. Preferably the amount of calcium carbonate exceeds the amount of DHEA, such as, for example, in a ratio of about 2.08 to 1 where the calcium carbonate and DHEA are provided multiples of an amount of 52 mg of calcium carbonate and 25 mg of DHEA per unit.

The plant rejuvenating mixture may be applied to the plant growth directly without harm to leaves or photosynthetic portions of the plant. The plant growth may be sprayed with the plant rejuvenating mixture by any convenient means, including spraying. The plant rejuvenating mixture may also be applied to the soil or infused, aerated, injected, and the like, into the soil surrounding the plants to be fertilized to a level sufficient to achieve the desired concentrations of the plant rejuvenating mixture in the soil.

The plant rejuvenating mixture may be applied more than once over a given period of time, depending on the nature of the soil, the environmental conditions, as well as other factors.

In still other embodiments, the plant rejuvenating mixture may be applied for a variety of uses, including, but not limited to, the mellowing of soil textural qualities; the enhancement of the decomposition of plant tissue; and the like. An additional use of the plant rejuvenating mixture includes applying the mixture to freshly cut flowers, typically for decorative uses, to retard senescence of the flowers. The mixture may be used in a dilute form to maintain the cut flowers.

EXAMPLES

The following examples are of tests which were conducted by the Applicant from 2000 through 2005.

Approximately 120 DHEA tablets, which contained per tablet 25 mg DHEA, 52 mg of calcium carbonate and trace amounts of cellulose, silica, magnesium stearate, and stearic acid, were combined with approximately 8 liters of hot (approx. 145 degrees F.) water to form a plant rejuvenating mixture. Once the DHEA was in mixture, the plant rejuvenating mixture was allowed to cool to room temperature. The plant rejuvenating mixture was then poured directly onto the plant soil of a spider plant (*Chlorophytum comosum*) until saturation with the plant rejuvenating mixture was reached. At that time the leaves of the spider plant were drooping with brown exudates and had probable root trouble. Approximately twenty hours later, the leaves had restored turgid pressure, and were a dark shade of green. The brown exudates were completely gone. Large new shoots were visible within ten days and subsequent cuttings were viable.

A Lucky bamboo plant (*Dracaena sanderiana*) was treated in a similar manner for root trouble. The plant had been kept in a small drinking glass and the roots were a darker color crowded in the bottom of the glass. In this example 40, 5 mg tablets of DHEA containing 38 mg of dicalcium phosphate and trace cellulose, silica, and magnesium stearate were added to 0.5 L hot water (approx. 145 degrees F.) and stirred to form a plant rejuvenating mixture. The plant rejuvenating mixture was cooled to room temperature and the bamboo plant was placed in a vase filled with this mixture. After one month the plant rejuvenating mixture was replaced with regular water for the plant and subsequent administrations of the plant rejuvenating mixture were limited to once per month. By the following summer the plant had reached 20 inches in height and the number of leaves tripled with each growing as high as 6 inches vertically.

Eighty DHEA tablets containing 38 mg of dicalcium phosphate and trace cellulose, silica, and magnesium stearate were added to 1 L hot water (approx. 160 degrees F.). After the initial mixture had formed, 2 L of cold water, at about 55 to 60 degrees Fahrenheit, preferably at a temperature ranging from 40 to 75 degrees F. were added to the 1 L initial mixture to form the plant rejuvenating mixture. The plant rejuvenating mixture was cooled to room temperature and then added to the soil of an Arabian Coffee Plant (*Coffea arabica*). Over the next three weeks four new leaves grew. The leaves appeared almost to have been polished. The plant rejuvenating mixture was made again using sixty tablets (rather than the original 80) and applied to the plant after transplantation six months after the original application.

Sixteen months later one of the two stalks was transferred to a separate pot and the soil was saturated in a similar manner with a plant rejuvenating mixture of fifty tablets. For the next two and one-half years the plant was exposed to low lighting and low temperatures during the cold months. After that time four leaves were left on the surviving stalk and those leaves were brittle and mottled with noticeable gray/brown spots. The plant rejuvenating mixture was again prepared for the plant using 100 tablets in 0.5 L of water. The tablets were placed in the water and the initial mixture was heated to 200 degrees Fahrenheit. The initial mixture was stirred and allowed to cool then diluted with 1.5 L of cold water to form the plant rejuvenating mixture. The cold water was supplied at about 55 to 60 degrees Fahrenheit, preferably at a temperature ranging from 40 to 75 degrees F. The plant rejuvenating mixture was poured onto the plant to saturation. During the subsequent eight weeks the four damaged leaves were replaced with eleven new leaves.

The plant rejuvenating mixture has also been used to treat rose bushes (*Rosa* sp.). Two rose bushes, originally contained in outdoor pots, displayed leaves with yellow patches and holes. New roses had not been produced for four weeks and parts of the stalks had turned from green to brown. The plant rejuvenating mixture was made using 100 DHEA tablets each containing 5 mg DHEA, 38 mg dicalcium phosphate, and trace amounts of cellulose, silica, and magnesium stearate. These tablets were placed in a beaker containing 0.5 L cold water, at about 55 to 60 degrees Fahrenheit, preferably at a temperature ranging from 40 to 75 degrees F. The water and tablets were heated to 168 degrees Fahrenheit and then transferred to a larger vessel to which 7.5 L of cold water was added. The resulting plant rejuvenating mixture was stirred, cooled and poured into each pot. This process was repeated every four days for approximately two months, into late fall. The roses were then placed under a protective canopy until spring. The roses produced blooms during the summer and into late October. A third rose bush, displaying similar maladies, was treated with plant rejuvenating mixture prepared with 80 rather than 100 tablets. This bush also survived the winter and grew roses the following summer. A fourth rose bush was treated using 70 tablets and application every five days. The fourth rose bush also survived the winter and then produced roses into October however fewer roses were produced and rose production stopped in mid rather than late October.

A Philodendron plant (*Philodendron* sp.) displayed flaccid leaves the majority of which were brown and brittle. Some of the leaves were yellow with black tips and the soil in the pot had a thin white crystalline crust over the surface. After removing the brown brittle leaves and leaving only the leaves that were yellow with black tips or green, a plant rejuvenating mixture was made using 100 DHEA tablets each containing 5 mg DHEA, 38 mg dicalcium phosphate, and trace amounts of cellulose, silica, and magnesium stearate. The tablets were added to 0.5 L water previously heated to 145 degrees Fahrenheit. The tablets were allowed to degrade for 10 minutes prior to adding 1.5 L cold water, at about 55 to 60 degrees Fahrenheit, preferably at a temperature ranging from 40 to 75 degrees F. The resulting plant rejuvenating mixture was then stirred and used to saturate the soil of the Philodendron. The remaining plant rejuvenating mixture was retained and administered monthly to the plant until the mixture was gone. The plant rejuvenating mixture was re-prepared in the same manner and applied monthly for the following twelve months. Although some of the yellow leaves died, most of the leaves regained full color with a darker shade of green than originally observed. The soil lost the white crust and the plant grew in size to the extent that it had to be transferred to a larger container. After the transfer, the Philodendron was intentionally neglected by providing random amounts of water, minimal sunlight, low temperatures, and winter transplantation.

Four months later the original symptoms were again noted. Cuttings of the plant were taken and placed into fresh pots with fresh soil. The plant rejuvenating mixture was prepared in a similar manner to the original preparation although the water was heated to 168 degrees Fahrenheit. The same method of application was used and the cuttings flourished despite exposure to low lighting and low temperatures (62 degrees Fahrenheit). The only treatments the plant received were water and monthly administration of the plant rejuvenating mixture.

A Blue Point Juniper Shrub (*Juniperus chinensis*) was the fifth shrub planted in an area adequate for only four shrubs, subjected to poor soil with poor drainage and neglected by landscapers. Fully half of the juniper turned a rich brown and lost its foliage down to the trunk. A plant rejuvenating mixture of 250 DHEA tablets each containing 5 mg DHEA, 38 mg dicalcium phosphate, and trace amounts of cellulose, silica, and magnesium stearate in 1 L of cold water was stirred and then heated to 200 degrees Fahrenheit, allowed to cool for 15 minutes and added to 7 L cold water. Cold water was supplied at about 55 to 60 degrees Fahrenheit, preferably at a temperature ranging from 40 to 75 degrees F. The resulting plant rejuvenating mixture was stirred again and then all 8 L were applied to the base of the shrub. A new plant rejuvenating mixture was prepared and applied each day for four days. The juniper survived and grew around the brown area, which became green and diminished in size by approximately fifteen percent. Six other Juniper bushes were found in the same condition. The plant rejuvenating mixture was prepared and applied in the same manner to these shrubs. Five of the shrubs survived, one of which grew around the brown area.

A turf grass blend including typically Kentucky bluegrass, ryegrass and tall fescue was also treated with plant rejuvenating mixture. The areas of turf grass had been covered for one month by planks. The sections were approximately three square feet and had been blocked from light and adequate water lending them a silver gray color and brittle texture. The turf grass appeared irretrievably damaged. Two hundred DHEA tablets were added to 1 L of hot water (approx. 170 degrees F.), stirred and allowed to cool for fifteen minutes prior to the addition of 6 L of cold water, at about 55 to 60 degrees Fahrenheit, preferably at a temperature ranging from 40 to 75 degrees F. The resulting plant rejuvenating mixture was again stirred and after thirty minutes, the entire plant rejuvenating mixture was poured onto the damaged sod saturating the area. This process was repeated daily for one week. During the next two weeks the turf grass grew fully in a darker green than the surrounding area. The turf grass in that location also grew back faster and taller than the surrounding grass.

Turf grass adversely affected by lawnmowers, dog urine and birds were also treated. In the case of the sections torn out by lawnmowers the same process of producing the plant rejuvenating mixture was use with varying doses, temperature and frequency of application. A dose of (100 to 400 tablets), temperatures (135 to 165 degrees F.), and frequency of application (6 to 7 days) appeared to produce the most expedient results (21 days to cover bald spots with grass). Lower doses (70 to 80 tablets), temperatures (115 to 120 degrees F.) and frequencies (4 to 5 days) covered with bald areas although the length of time required was greater (42 days). Much lower doses (50 to 60 tablets) in room temperature water applied for only 2 to 3 days produced negligible results. Dog urine spots were best treated with 100 tablets in hot water of 170 degrees F. and administered daily produced the most expedient return to pre-urine color (10-14 days). The area of turf grass destroyed by birds was treated with 100 tablets of DHEA added to 0.5 L of 200 degree Fahrenheit water, stirred and diluted with 7.5 L of cold water, at about 55 to 60 degrees Fahrenheit, preferably at a temperature ranging from 40 to 75 degrees F., which after 30 minutes was added in full to the destroyed area. This process was repeated for four days and then only once per month for four months. The area fully regained its green color.

Based upon the above, the amount of DHEA applied is preferably in range of from about 200 mg to about 1000 mg per liter of water. For example, according to the aforesaid tested examples, DHEA is applied as follows:

a) to the spider plant is applied 4 gms DHEA to 4 gallons of water=15.14 liters ([or 1 gm per gallon=250 mg per quart or 237 mg per liter];
b) to the Coffee plant is applied 400 mg DHEA in one liter water;
c) to the Philodendron plant is applied 300 mg DHEA and one liter of water;
d) to the Juniper shrub is applied 1000 mg DHEA (one gram) and one quart of water=0.95 liter;
e) to the rose plant is applied 400 mg DHEA and one quart of water=0.95 liter;
f) to the Turf grass is applied 1000 mg DHEA and one quart of water=0.95 liter;

It should be understood that the foregoing descriptions are only illustrative of the disclosure. Various alternatives and modifications can be devised by those skilled in the art without departing from the disclosure. Accordingly, the present disclosure and invention is intended to embrace all such alternatives, modifications and variances, which fall within the scope of the appended claims.

What is claimed is:

1. A method for preparing a plant rejuvenating mixture for a stressed and/or wilted plant comprising the steps of:
providing a rejuvenating ingredient including dehydroepiandrosterone (DHEA) or hydrates thereof;
providing a liquid selected from the group consisting of water and fertigation liquids; and
combining said rejuvenating ingredient with said liquid to form a plant rejuvenating mixture for a stressed and/or wilted plant; wherein said rejuvenating ingredient further includes at least one nutrient.

2. The method of claim 1 wherein said at least one nutrient is the micronutrient calcium.

3. The method of claim 2 wherein said calcium is supplied as calcium carbonate.

4. The method of claim 2 wherein said calcium is supplied as dicalcium phosphate.

5. The method of claim 1 wherein said at least one nutrient is the macronutrient phosphorus.

6. The method of claim 5 wherein said phosphorus is supplied as dicalcium phosphate.

7. The method of claim 1 wherein said DHEA is provided in an amount of from about 200 mg DHEA per liter of water to about 1000 mg DHEA per liter of water.

8. A method of claim 3 wherein said rejuvenating ingredient is provided in the form of a tablet including about 18% DHEA and about 82% calcium carbonate, said amount of water is heated to about 145 degrees Fahrenheit, said rejuvenating mixture is formed by stirring said tablet in the water to disperse the rejuvenating ingredients in the water, and said rejuvenating mixture is further allowed to cool to room temperature.

9. The method of claim 4 wherein said rejuvenating ingredient is provided in the form of a tablet including about 12% DHEA and about 88% dicalcium phosphate, said amount of water being heated to about 145 degrees Fahrenheit, said rejuvenating mixture is formed by stirring said tablet in the water to disperse the rejuvenating ingredients in the water, and said rejuvenating mixture is further allowed to cool to room temperature.

10. The method of claim 1, wherein said rejuvenating ingredient is provided in the form of a tablet and is combined with water in a ratio of 40 DHEA tablets containing macronutrients and trace micronutrients, said tablets containing 5 mg DHEA, 38 mg dicalcium phosphate, and trace amounts of silica, cellulose and magnesium stearate, to 0.5 L tap water, said water being heated to about 145 degrees Fahrenheit, to form the rejuvenating mixture, said rejuvenating mixture is formed by stirring said tablet in the water to disperse the rejuvenating ingredients in the water, and said rejuvenating mixture is further allowed to cool to room temperature.

11. The method of claim 1, wherein said rejuvenating ingredient is provided in the form of a tablet and is combined with water in a ratio of 80 DHEA tablets containing macronutrients and trace micronutrients, said tablets containing 5 mg DHEA, 38 mg dicalcium phosphate, and trace amounts of silica, cellulose and magnesium stearate per tablet, to 1 L tap water said water being heated to about 160 degrees Fahrenheit, to form the rejuvenating mixture, said rejuvenating mixture is formed by stirring said tablet in the water to disperse the rejuvenating ingredients in the water, and said rejuvenating mixture is further allowed to cool to room temperature.

12. The method of claim 1, wherein said rejuvenating ingredient is provided in the form of a tablet and is combined with water in a ratio of 60 DHEA tablets containing macronutrients and trace micronutrients, said tablets containing 5 mg DHEA, 38 mg dicalcium phosphate, and trace amounts of silica, cellulose and magnesium stearate per tablet, to 1 L tap water said water being heated to about 160 degrees Fahrenheit, to form the rejuvenating mixture, said rejuvenating mixture is formed by stirring said tablet in the water to disperse the rejuvenating ingredients in the water, and said rejuvenating mixture is further allowed to cool to room temperature.

13. The method of claim 1, wherein said rejuvenating ingredient is provided in the form of a tablet and is combined with water in a ratio of 50 DHEA tablets containing macronutrients and trace micronutrients, said tablets containing 5 mg DHEA, 38 mg dicalcium phosphate, and trace amounts of silica, cellulose and magnesium stearate per tablet, to 1 L tap water said water being heated to about 160 degrees Fahrenheit, to form the rejuvenating mixture, said rejuvenating mixture is formed by stirring said tablet in the water to disperse the rejuvenating ingredients in the water, and said rejuvenating mixture is further allowed to cool to room temperature.

14. The method of claim 1, further comprising the step of:
diluting the rejuvenating mixture with 3 times the initial amount of water.

15. The method of claim 14, wherein said rejuvenating ingredient is provided in the form of a tablet and is combined with water in a ratio of 100 DHEA tablets containing macronutrients and trace micronutrients, said tablets containing 5 mg DHEA, 38 mg dicalcium phosphate, and trace amounts of silica, cellulose and magnesium stearate per tablet, to 0.5 L tap water, said water being heated to about 200 degrees Fahrenheit, to form the rejuvenating mixture, said rejuvenating mixture is formed by stirring said tablet in the water to disperse the rejuvenating ingredients in the water, and said rejuvenating mixture is further allowed to cool to room temperature, said rejuvenating mixture is then diluted with an additional 1.5 L of cold water, at about 55 to 60 degrees Fahrenheit, at a temperature ranging from about 40 to about 75 degrees F.

16. The method of claim 14, wherein said rejuvenating ingredient is provided in the form of a tablet and is combined with water in a ratio of 100 DHEA tablets containing macronutrients and trace micronutrients, said tablets containing 5 mg DHEA, 38 mg dicalcium phosphate, and trace amounts of silica, cellulose and magnesium stearate per tablet, to 0.5 L tap water, said water being heated to about 145 degrees Fahrenheit, to form the rejuvenating mixture, said rejuvenating mixture is formed by stirring said tablet in the water to disperse the rejuvenating ingredients in the water, and said rejuvenating mixture is further allowed to cool to room temperature, then diluting said mixture with an additional 1.5 L of cold water, provided at a temperature ranging from 40 to 75 degrees F.

17. The method of claim 14, wherein said rejuvenating ingredient is provided in the form of a tablet and is combined with water in a ratio of 100 DHEA tablets containing macronutrients and trace micronutrients, said tablets containing 5 mg DHEA, 38 mg dicalcium phosphate, and trace amounts of silica, cellulose and magnesium stearate per tablet, to 0.5 L tap water said water being heated to about 168 degrees Fahrenheit, to form the rejuvenating mixture, said rejuvenating mixture is formed by stirring said tablet in the water to disperse the rejuvenating ingredients in the water, and said rejuvenating mixture is further allowed to cool to room temperature, then diluting said mixture with an additional 1.5 L of cold water, provided at a temperature ranging from 40 to 75 degrees F.

18. The method of claim 1, further comprising the step of:
diluting the rejuvenating mixture with 15 times the initial amount of water.

19. The method of claim 18, wherein said rejuvenating ingredient is provided in the form of a tablet and is combined with water in a ratio of 100 DHEA tablets containing macronutrients and trace micronutrients, said tablets containing 5 mg DHEA, 38 mg dicalcium phosphate, and trace amounts of silica, cellulose and magnesium stearate per tablet, to 0.5 L tap water, an initial mixture is formed by adding the tablets to the water and the tablets and water are heated to about 168 degrees Fahrenheit, said heated rejuvenating mixture is further transferred to an 8 L container and 7.5 L cold water provided at a temperature ranging from 40 to 75 degrees F. is added, the cooled rejuvenating mixture is stirred to form the final rejuvenating mixture, said final rejuvenating mixture is formed by stirring to disperse the rejuvenating ingredients in the water, and said final rejuvenating mixture is further allowed to cool to room temperature.

20. The method of claim 18 wherein said rejuvenating ingredient is provided in the form of a tablet and is combined with water in a ratio of 80 DHEA tablets containing macronutrients and trace micronutrients, said tablets containing 5 mg DHEA, 38 mg dicalcium phosphate, and trace amounts of silica, cellulose and magnesium stearate per tablet, to 0.5 L tap water, an initial mixture is formed by adding the tablets to the water and the tablets and water are heated to about 168 degrees Fahrenheit, said heated rejuvenating mixture is further transferred to an 8 L container and 7.5 L cold water provided at a temperature ranging from 40 to 75 degrees F. is added, said final rejuvenating mixture is formed by stirring to disperse the rejuvenating ingredients in the water, and said final rejuvenating mixture is further allowed to cool to room temperature.

21. The method of claim 1, wherein said rejuvenating ingredient is in the form of a tablet and combined with water and heated to about 200 degrees Fahrenheit, said rejuvenating mixture is further allowed to cool, then said rejuvenating mixture is diluted with 7 times the initial amount of water and stirred.

22. The method of claim 21 wherein said rejuvenating ingredient is provided in the form of a tablet and is combined with water in a ratio of 250 DHEA tablets containing macronutrients and trace micronutrients, said tablets containing 5 mg DHEA, 38 mg dicalcium phosphate, and trace amounts of silica, cellulose and magnesium stearate per tablet, to 1 L tap water, an initial mixture is formed by adding the tablets to the water and the tablets and water are heated to about 200 degrees Fahrenheit, said heated rejuvenating mixture is further transferred to an 8 L container and 7 L cold water provided at a temperature ranging from 40 to 75 degrees F. is added, the cooled rejuvenating mixture is stirred to form the final rejuvenating mixture, said final rejuvenating mixture is formed by stirring to disperse the rejuvenating ingredients in the water, and said final rejuvenating mixture is further allowed to cool to room temperature.

23. The method of claim 1, wherein the rejuvenating mixture is applied to treat and inhibit plant decomposition and disease comprising contacting the plant soil, leaves, or stems with the rejuvenating mixture.

24. The method of claim 19, wherein said rejuvenating ingredient is provided in the form of a tablet and is combined with water in a ratio of 120 DHEA tablets, which contain per tablet 25 mg DHEA, 52 mg of calcium carbonate and trace amounts of cellulose, silica, magnesium stearate, and stearic acid, and initial mixture being combined with approximately 8 liters of hot water to form said rejuvenating mixture, said rejuvenating mixture being allowed to cool to room temperature.

25. The method of claim 23 wherein the rejuvenating mixture is sprayed on the plants and soil.

26. The method of claim 23 wherein the rejuvenating mixture is applied to the soil surrounding the plants.

27. A method of claim 25 wherein the rejuvenating mixture is applied to cut flowers and greens.

28. The method as in claim 1 further comprising the step of heating said liquid.

29. The method of claim 28 wherein said water is heated to about 145 degrees Fahrenheit.

30. The method as in claim 29 wherein said heated water is cooled by cold water provided at a temperature ranging from about 40 to about 75 degrees F.

31. The method as in claim 28 further comprising the step of allowing said heated plant rejuvenating liquid to cool to a tepid level.

32. A method of rejuvenating a stressed and/or wilted plant comprising the steps of:
  a) providing a rejuvenating ingredient including:
    dehydroepiandrosterone (DHEA) or hydrate thereof, and
    essential plant nutrients of either or both of calcium and phosphorus, wherein said nutrients are supplied in an amount sufficient for plant rejuvenation;
  b) adding said rejuvenating ingredient to a liquid selected from the group consisting of water and fertigation liquids;
  c) forming a plant rejuvenating mixture therefrom; and,
  d) applying the plant rejuvenating mixture to the plant.

33. The method of claim 32 wherein the plant rejuvenating mixture is applied to soil in which the plant is rooted.

34. The method of claim 32 wherein the plant rejuvenating mixture is applied directly to photosynthetic portions of the plant.

35. The method of claim 34 wherein said plant rejuvenating mixture is applied by spraying.

36. The method of claim 32 wherein said nutrients are supplied as dicalcium phosphate.

37. The method of claim 32 wherein said phosphorus is supplied as dicalcium phosphate.

38. The method of claim 32 wherein said calcium is supplied as calcium carbonate.

39. The method of claim 32 wherein said calcium is supplied as dicalcium phosphate.

40. The method of claim 32 in which said plant is a spider plant and the plant rejuvenating mixture containing nutrient calcium carbonate is poured directly on plant soil thereof until saturation is reached.

41. The method of claim 32 in which said plant is *Dracaena sanderiana* and the plant rejuvenating mixture contains dicalcium phosphate.

42. The method of claim 32 in which said plant is a rose bush and the plant rejuvenating mixture contains dicalcium phosphate.

43. The method of claim 32 in which said plant is a Philodendron and the plant rejuvenating mixture contains dicalcium phosphate, said plant rejuvenating mixture saturates the soil in which said plant is rooted, and is applied monthly until leaves of said plant regain full color.

44. The method of claim 32 in which said plant is a *Juniperus chinensis* and the plant rejuvenating mixture contains dicalcium phosphate, said plant rejuvenating mixture being applied to a base of said plant, applying a new plant rejuvenating mixture each day for a number of days.

45. The method of claim 32 in which said plant is a turf grass blend including Kentucky bluegrass, ryegrass, and tall fescue.

46. The method of claim 32 in which said plant is *Coffee arabica* and the plant rejuvenating mixture contains dicalcium phosphate.

47. The method of claim 32 wherein said nutrients are supplied in an amount which exceeds by weight that of the DHEA.

48. The method of claim 35 wherein the ratio of said dicalcium phosphate to DHEA is about 7.6 to 1.

49. The method of claim 36 wherein the ratio of said calcium carbonate to DHEA is about 2.08 to 1.

50. The method as in claim 32 further comprising the step of heating said liquid.

51. The method as in claim 50 further comprising the step of allowing said heated plant rejuvenating liquid to cool to a tepid level.

* * * * *